(12) United States Patent
Kara et al.

(10) Patent No.: US 9,157,085 B2
(45) Date of Patent: Oct. 13, 2015

(54) EXPRESSION VECTOR FOR EXPRESSION OF EUKARYOTIC SECRETION LEADER SEQUENCE FUSED WITH A TARGET POLYPEPTIDE AND METHODS OF USE THEREOF

(75) Inventors: Bhupendra Vallabh Kara, Billingham (GB); Christopher David John Lennon, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 0 days.

(21) Appl. No.: 12/995,924

(22) PCT Filed: Jun. 1, 2009

(86) PCT No.: PCT/GB2009/001372
§ 371 (c)(1),
(2), (4) Date: Dec. 2, 2010

(87) PCT Pub. No.: WO2009/147382
PCT Pub. Date: Dec. 10, 2009

(65) Prior Publication Data
US 2011/0086391 A1    Apr. 14, 2011

(30) Foreign Application Priority Data
Jun. 4, 2008    (GB) .................................. 0810154.5

(51) Int. Cl.
*C12N 15/62*    (2006.01)
*C12N 15/70*    (2006.01)

(52) U.S. Cl.
CPC .............. *C12N 15/625* (2013.01); *C12N 15/70* (2013.01)

(58) Field of Classification Search
USPC ............................................................ 435/6
See application file for complete search history.

(56) References Cited

U.S. PATENT DOCUMENTS

| | | | | |
|---|---|---|---|---|
| 6,403,782 B1 * | 6/2002 | Luster et al. | ................. | 536/23.5 |
| 6,537,779 B1 * | 3/2003 | Kara et al. | ................. | 435/69.1 |
| 8,394,937 B2 * | 3/2013 | Kara et al. | ................. | 536/23.1 |

(Continued)

FOREIGN PATENT DOCUMENTS

| | | | |
|---|---|---|---|
| GB | WO2007/088371 | * | 8/2007 |
| WO | WO 03/068956 | | 8/2003 |

OTHER PUBLICATIONS

Schein et al., Secretion of mammalian ribonucleases from *Escherichia coli* using the signal sequence of murine spleen ribonuclease. Biochem. J., (1992), vol. 283, pp. 137-144.*

(Continued)

*Primary Examiner* — Alexander Kim
(74) *Attorney, Agent, or Firm* — Morgan, Lewis & Bockius LLP

(57) ABSTRACT

An expression vector for expressing a target polypeptide in a prokaryotic cell is provided. The vector comprises a promoter operably linked to a polynucleotide encoding the target polypeptide operably linked to a eukaryotic secretion leader sequence, the eukaryotic secretion leader sequence encoding a signal peptide sequence selected from the group consisting of: a) MLKRSSWLATLGLLTVASVSTIVYA; b) MKKATFITCLLAVLLVSNPIWNA; c) MKVSAAALAVILIATALCAPASA; d) MKVSTAFLCLLLTVSAFSAQVLA; and e) MKCLLLALGLALACAAQA. Processes for expressing polypeptides and prokaryotic microorganisms comprising such vectors are also provided.

16 Claims, 6 Drawing Sheets

SDS-PAGE analysis of shake-flask evaluation of Strain 1

| Lane | Sample |
|---|---|
| 1 | Mol wt markers |
| 2 | Strain 1 Supernatant/Growth medium |
| 3 | Strain 1 OS1 fraction |
| 4 | Strain 1 OS2 fraction |
| 5 | Strain 1 Cell pellet fraction |

TAR1-5-19

(56) References Cited

U.S. PATENT DOCUMENTS

| | | |
|---|---|---|
| 8,530,188 B2 * | 9/2013 | Kara et al. .................. 435/69.1 |
| 2008/0070300 A1 * | 3/2008 | Ponath et al. ................ 435/331 |

OTHER PUBLICATIONS

Rothenberg et al., Constitutive and allergen-induced expression of eotaxin mRNA in the guinea pig lung., J Exp Med., (1995), vol. 181(3), pp. 1211-1216.*

Choi et al., Secretory and extracellular production of recombinant proteins using *Escherichia coli*., Appl Microbiol Biotechnol (2004), vol. 64, pp. 625-635.*

Kitaura et al., Molecular Cloning of Human Eotaxin, an Eosinophil-selective CC Chemokine, and Identification of a Specific Eosinophil Eotaxin Receptor, CC Chemokine Receptor 3., The Journal of Biological Chemistry (1996), vol. 271, pp. 7725-7730.*

Araki et al., Cloning, Sequencing, and Expression in *Escherichia coli* of the New Gene Encoding β-1,3-Xylanase from a Marine Bacterium, *Vibrio* sp. Strain XY-214., Appl Environ Microbiol. (2000), vol. 66(4), pp. 1741-1743.* pBluescript II KS sequence and map (last viewed on Sep. 24, 2013).* pBluescript II Phagemid Vectors Instruction Manual (last viewed on Sep. 24, 2013).* pBacPAK9 Vector Information, published Aug. 6, 2002.*

Talmadge et al. (Eukaryotic signal sequence transports insulin antigen in *Escherichia coli*., Proc. Natl. Acad. Sci USA (1980), vol. 77, pp. 3369-3373).*

Nakamura et al., Variant eotaxin: Its effects on the asthma phenotype., Journal of Allergy and Clinical Immunology (2001), vol. 108, pp. 946-953.*

Sinden et al., Perfect palindromic lac operator DNA seqeunce exists as a stable cruciforom structure in supercoiled DNA in vitro but not in vivo., Proc. Natl. Acad. Sci. USA (1983), vol. 80, pp. 1797-1801.*

Simons et al., Possible ideal lac operator: *Escherichia coli* lac operator-like sequences from eukaryotic genomes lack the central G X C pair. Proc Natl Acad Sci U S A. (1984), vol. 81(6), pp. 1624-1628.*

Berlin, Functional Activity of Eukaryotic Signal Sequences in *Escherichi coli*: teh Ovalbumin Family of Serine Protease Inhibitors . . . , J. Mol. Biol, 335, 437-453, 2004.

Humphreys, High-Level Periplasmic Expression in *Escherichia coli* Using a Eukaryotic Signal Peptide . . . , Protein Expression and Purification, 20, 252-264, 2000.

* cited by examiner

Figure 1. SDS-PAGE analysis of shake-flask evaluation of Strain 1
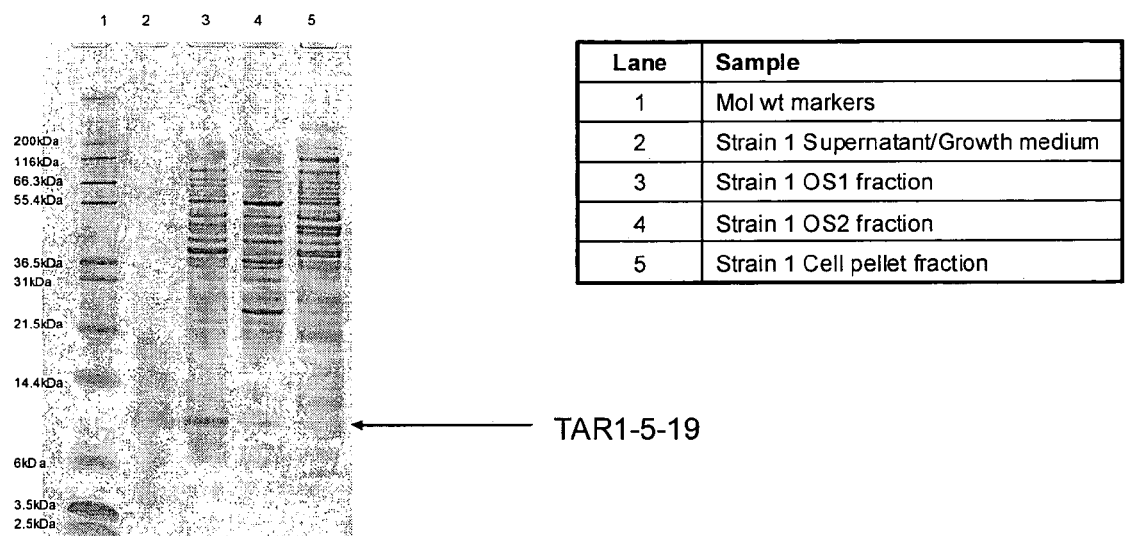

Figure 2. SDS-PAGE analysis of shake-flask evaluation of Strain 2
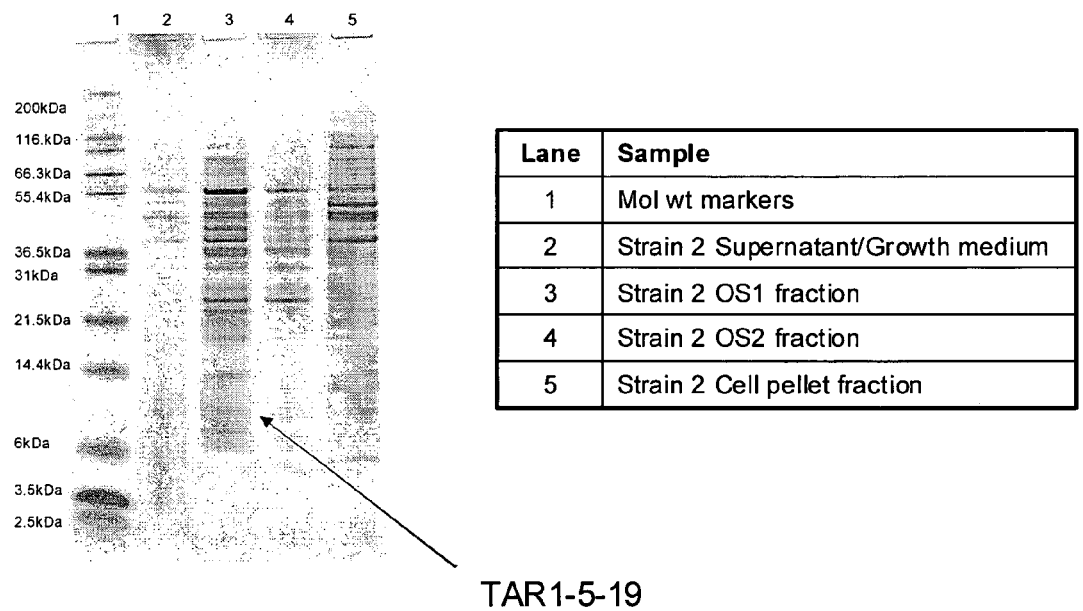
| Lane | Sample |
|------|--------|
| 1 | Mol wt markers |
| 2 | Strain 2 Supernatant/Growth medium |
| 3 | Strain 2 OS1 fraction |
| 4 | Strain 2 OS2 fraction |
| 5 | Strain 2 Cell pellet fraction |
TAR1-5-19
Figure 3. SDS-PAGE analysis of shake-flask evaluation of Strain 3
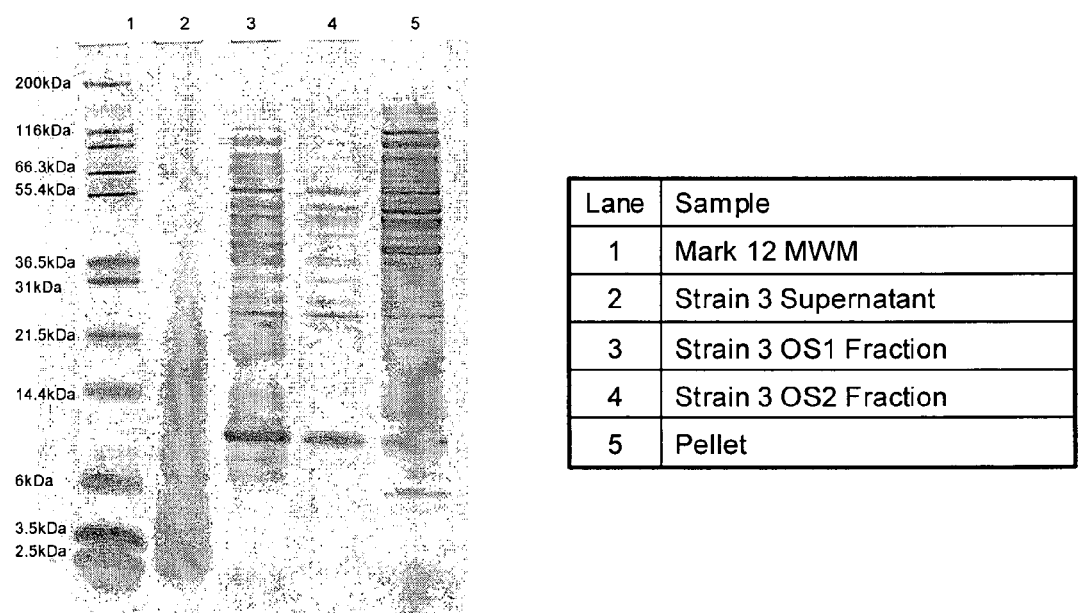
| Lane | Sample |
|------|--------|
| 1 | Mark 12 MWM |
| 2 | Strain 3 Supernatant |
| 3 | Strain 3 OS1 Fraction |
| 4 | Strain 3 OS2 Fraction |
| 5 | Pellet |

Figure 4. SDS-PAGE analysis of shake-flask evaluation of Strain 5 and Strain 6
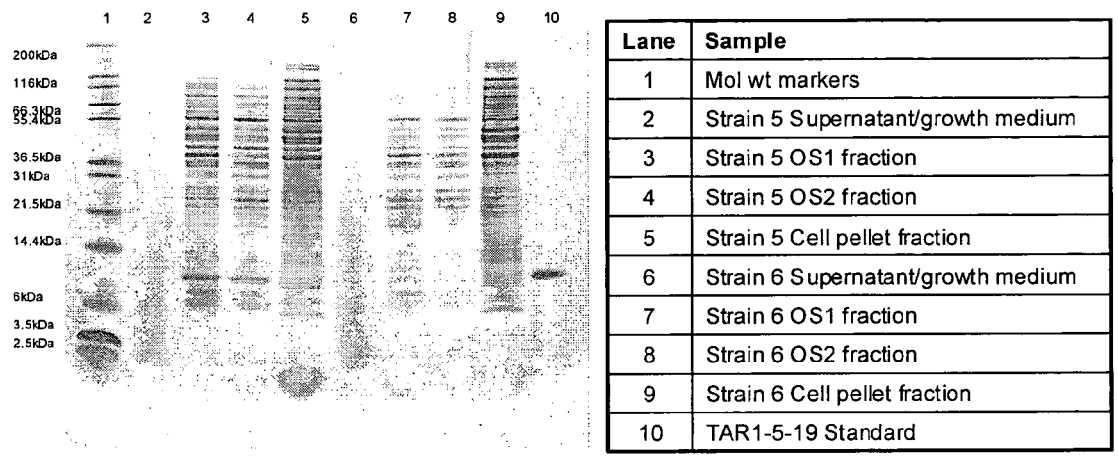
Figure 5. SDS-PAGE analysis of shake-flask evaluation of Strain 7 and Strain 8
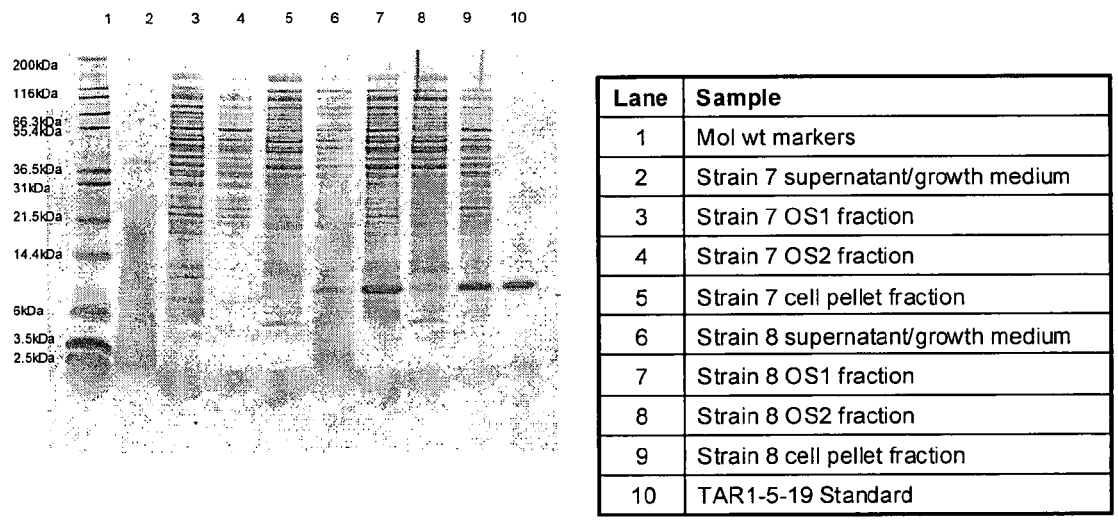

Figure 6. SDS-PAGE analysis of fermentation analysis of Strain 1

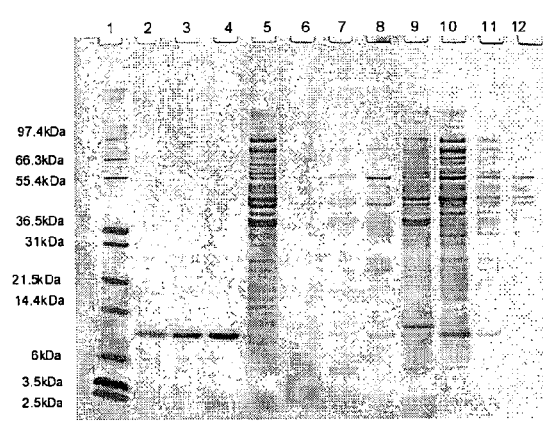

| Lane | Sample |
|---|---|
| 1 | Mark 12 MWM |
| 2 | 0.5µg loading TAR1-5-19 standard |
| 3 | 1.0µg loading TAR1-5-19 standard |
| 4 | 1.5µg loading TAR1-5-19 standard |
| 5 | Pre-induction Pellet |
| 6 | Pre-induction S/N |
| 7 | Pre-induction OS1 |
| 8 | Pre-induction OS2 |
| 9 | 46 Hours post-induction Pellet |
| 10 | 46 Hours post-induction S/N |
| 11 | 46 Hours post-induction OS1 |
| 12 | 46 Hours post-induction OS2 |

Figure 7. SDS-PAGE analysis of fermentation analysis of Strain 3

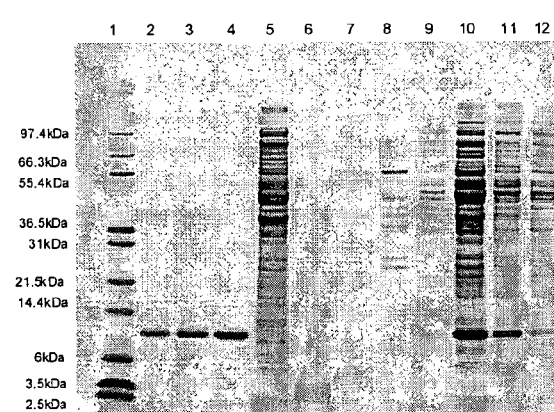

| Lane | Sample |
|---|---|
| 1 | Mark 12 MWM |
| 2 | 0.5µg loading TAR1-5-19 standard |
| 3 | 1.0µg loading TAR1-5-19 standard |
| 4 | 1.5µg loading TAR1-5-19 standard |
| 5 | Pre-induction Pellet |
| 6 | Pre-induction S/N |
| 7 | Pre-induction OS1 |
| 8 | Pre-induction OS2 |
| 9 | 46 Hours post-induction Pellet |
| 10 | 46 Hours post-induction S/N |
| 11 | 46 Hours post-induction OS1 |
| 12 | 46 Hours post-induction OS2 |

Figure 8 Secretion of Thioredoxin by Strains 9, 10 and 11

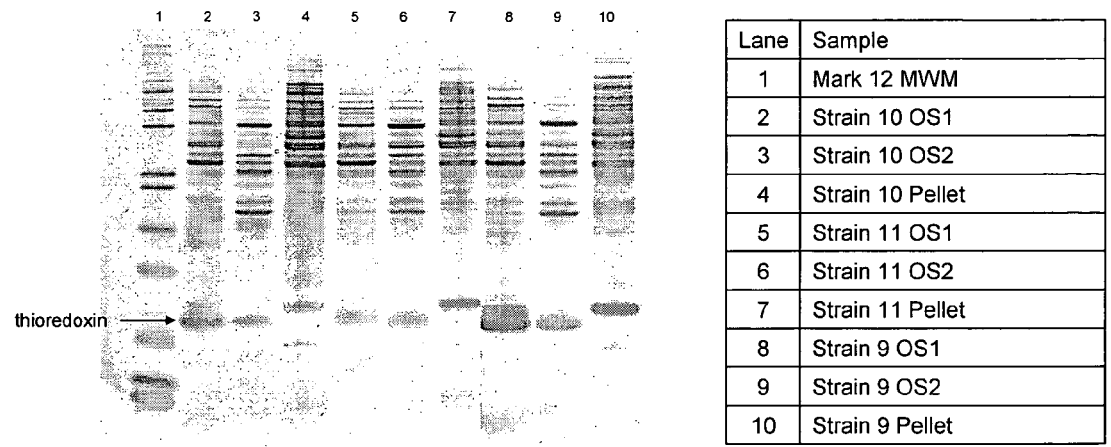

| Lane | Sample |
|---|---|
| 1 | Mark 12 MWM |
| 2 | Strain 10 OS1 |
| 3 | Strain 10 OS2 |
| 4 | Strain 10 Pellet |
| 5 | Strain 11 OS1 |
| 6 | Strain 11 OS2 |
| 7 | Strain 11 Pellet |
| 8 | Strain 9 OS1 |
| 9 | Strain 9 OS2 |
| 10 | Strain 9 Pellet |

Figure 9. Secretion of Human Growth Hormone by Strain 12

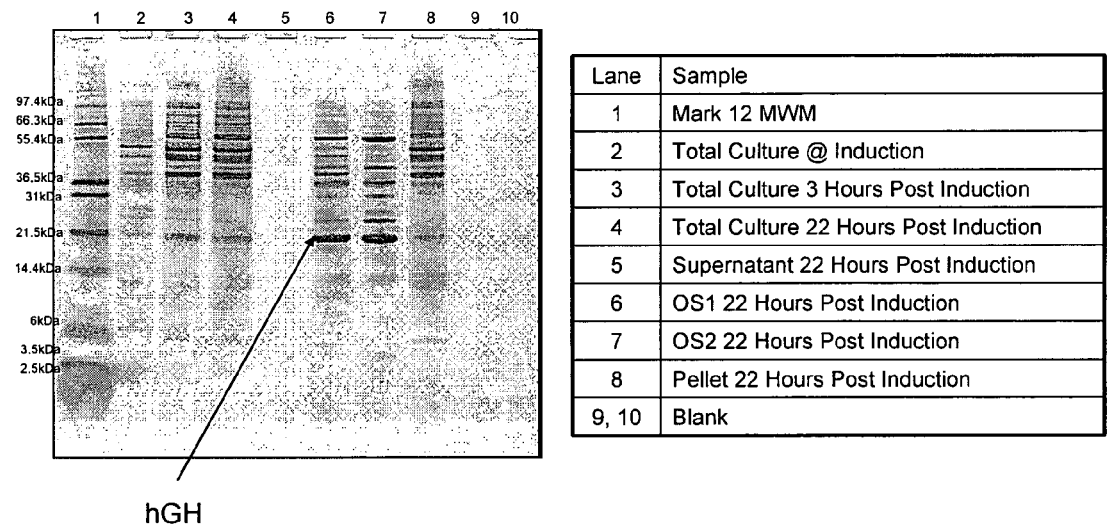

| Lane | Sample |
|---|---|
| 1 | Mark 12 MWM |
| 2 | Total Culture @ Induction |
| 3 | Total Culture 3 Hours Post Induction |
| 4 | Total Culture 22 Hours Post Induction |
| 5 | Supernatant 22 Hours Post Induction |
| 6 | OS1 22 Hours Post Induction |
| 7 | OS2 22 Hours Post Induction |
| 8 | Pellet 22 Hours Post Induction |
| 9, 10 | Blank |

Figure 10 Secretion of Thioredoxin by *Pseudomonas putida*
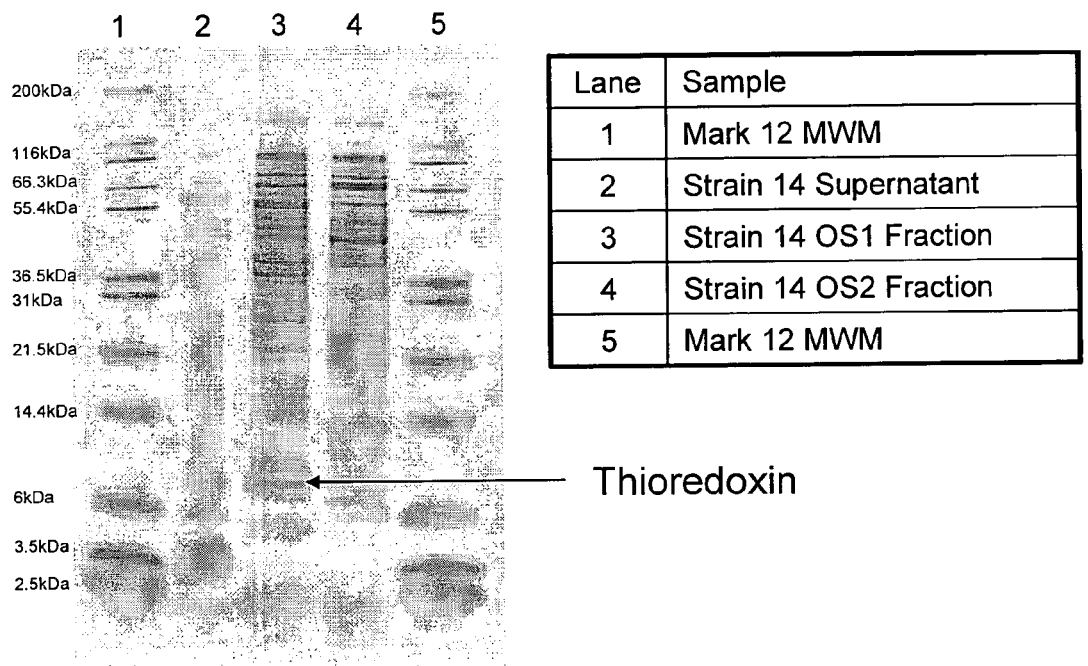

EXPRESSION VECTOR FOR EXPRESSION OF EUKARYOTIC SECRETION LEADER SEQUENCE FUSED WITH A TARGET POLYPEPTIDE AND METHODS OF USE THEREOF

RELATED APPLICATIONS

The present application is a U.S. National Phase Application of International Application No. PCT/GB2009/001372 (filed Jun. 1, 2009) which claims priority to Great Britain Patent Application No. 0810154.5 (filed Jun. 4, 2008) which are hereby incorporated by reference in their entirety.

SEQUENCE LISTING SUBMISSION VIA EFS-WEB

A computer readable text file, entitled "056258-5136_SequenceListing.txt," created on or about Dec. 2, 2010 with a file size of about 13 kb contains the sequence listing for this application and is hereby incorporated by reference in its entirety.

EXPRESSION VECTOR

The present invention concerns a process for the expression of a polypeptide in a prokaryotic cell using eukaryotic secretion leader sequences.

It is of significant benefit in recombinant polypeptide production if the polypeptide of interest can be exported from the cell in which it is expressed. Expression systems are therefore advantageously designed to enable such export, or secretion. Secretion of the recombinant polypeptide from the host cell commonly involves use of signal peptides, which are found on the majority of eukaryotic and prokaryotic proteins that are destined for export from the cytoplasm. Signal peptides employed in such expression systems are typically native to the expression host, for example, the PhoA, MalB and OmpA signal peptides of *Escherichia coli* have been used extensively to secrete polypeptides to the periplasm of that organism. As a matter of course, the use of prokaryotic hosts involves the use of prokaryotic signal peptides. Prokaryotic secretion leader sequences encoding suitable signal peptides are therefore commonly included in prokaryotic expression systems.

The expression of eukaryotic proteins using prokaryotic expression hosts often leads to highly unpredictable and inconsistent secretion of recombinant polypeptides. The use of many eukaryotic signal peptides in different systems results in expression systems which are inefficient, with low yields being commonplace. In addition, problems may be encountered with the misprocessing of the signal peptide, which may be improperly removed or incompletely cleaved. Thus there is a need for eukaryotic secretion signal peptides that result in efficient expression and secretion of recombinant polypeptides in prokaryotic hosts.

BRIEF DESCRIPTION OF DRAWINGS

FIG. 1 shows SDS-PAGE analysis results of shake-flask evaluation of Strain 1.

FIG. 2 shows SDS-PAGE analysis results of shake-flask evaluation of Strain 2.

FIG. 3 shows SDS-PAGE analysis results of shake-flask evaluation of Strain 3.

FIG. 4 shows SDS-PAGE analysis results of shake-flask evaluation of Strains 5 and 6.

FIG. 5 shows SDS-PAGE analysis results of shake-flask evaluation of Strains 7 and 8.

FIG. 6 shows SDS-PAGE analysis results of fermentation analysis of Strain 1.

FIG. 7 shows SDS-PAGE analysis results of fermentation analysis of Strain 3.

FIG. 8 depicts secretion of thioredoxin by Strains 9, 10 and 11.

FIG. 9 depicts secretion of human growth hormone by Strain 12.

FIG. 10 depicts secretion of thioredoxin by Pseudomonas Dutida.

According to one aspect of the present invention, there is provided an expression vector for expressing a target polypeptide in a prokaryotic cell, comprising a promoter operably linked to a polynucleotide encoding a target polypeptide operably linked to a eukaryotic secretion leader sequence, the eukaryotic secretion leader sequence encoding a signal peptide sequence selected from the group consisting of:

| a) | MLKRSSWLATLGLLTVASVSTIVYA; | (SEQ ID NO 1) |
|---|---|---|
| b) | MKKATFITCLLAVLLVSNPIWNA; | (SEQ ID NO 2) |
| c) | MKVSAAALAVILIATALCAPASA; | (SEQ ID NO 3) |
| d) | MKVSTAFLCLLLTVSAFSAQVLA; and | (SEQ ID NO 4) |
| e) | MKCLLLALGLALACAAQA | (SEQ ID NO 5) | or a functional equivalent thereof.

A functionally equivalent signal peptide is one that shares 70% or greater identity with an amino acid sequence, preferably 75% or greater identity, more preferably 80% or greater identity and most preferably 90% or greater identity, such as 95% identity or more, and which retains the ability to secrete the target polypeptide from a prokaryotic cell.

In many embodiments, DNA sequences which are operably linked are contiguous and, in the case of a secretion leader, contiguous and in the same reading frame.

Preferably, the linkage between the secretion leader sequence and the polynucleotide encoding the target polypeptide is such that the signal peptide sequence is attached to the N-terminal of the target polypeptide. In certain embodiments, the target polypeptide comprises an N-terminal tag, the linkage between the secretion leader sequence and the polynucleotide encoding the target polypeptide being such that the signal peptide sequence being attached to the tag, preferably to the N-terminus of the tag.

Polynucleotides comprising a nucleotide sequence encoding a signal peptide with amino acid sequences (SEQ ID NO 1), (SEQ ID NO 2), (SEQ ID NO 3), (SEQ ID NO 4) or (SEQ ID NO 5), or a functional equivalent thereof, operably linked to a nucleotide sequence encoding a recombinant polypeptide form a further aspect of the present invention.

The eukaryotic secretion leader sequence is preferably attached at the 5' end of the polynucleotide encoding the target polypeptide. The nucleotide encoding signal peptide a) preferably has the sequence CATATGCTGAAACGTTCTTCTTGGCTGG CAACTCTGGGTCTGCTGACTGTTGCATCCGTAAGCACTATTGTGTATGCA (SEQ ID NO 6). The nucleotide encoding signal peptide b) preferably has the sequence CATATGAAGAAAGCTACGTTTATTACTTGCCTGCTGGCTGTTCTGCTGGTTTCTAACC CGATCGTTGTTAACGCG (SEQ ID NO 7). The nucleotide encoding signal peptide c) preferably has the sequence CATATGAAAGTGTCTGCGGCCGCACTGGCA GTAATCCTGATCGCAACTGCGCTGT-GCGCGCCAGCCAGCGCA (SEQ ID NO 8). The nucleotide encoding signal peptide d) preferably has the sequence CATATGAAAGTTTCTACTGCATTTCTGT-GTCTGCTGCTGACTGTTAGCGCATTCTCCG CTCAG-GTCCTGGCC (SEQ ID NO 9). The nucleotide encoding signal peptide e) preferably has the sequence CATAT-GAAATGTCTGCTGCTGGCGCTGGGTCTGGC ACTG-GCATGTGCGGCACAGGCG (SEQ ID NO 10).

Promoters which may be employed in the vectors according to the present invention comprise constitutive or inducible promoters. In many preferred embodiments, the promoter is a prokaryotic promoter. Examples of prokaryotic promoters that can be employed include:

a) phage RNA polymerase-dependent promoters, particularly T7 RNA polymerase-dependent promoter systems, preferably single T7 promoters, including those disclosed by Studier and Moffat, J. Mol. Biol. 189:113-130 (1986), incorporated herein by reference, especially a T7 gene 10 promoter; and b) host RNA polymerase-based promoter systems, especially *E. coli* RNA polymerase-based promoter systems.

Examples of preferred promoters which can be employed include T7 gene 10 promoter, T7A1, T7A2, T7A3, λpL, λpR, lac, lacUV5, trp, tac, trc, phoA and rrnB.

When a T7 RNA-polymerase dependent promoter system is employed, it will be recognised that a source of T7 RNA polymerase is required, which is provided by methods known in the art, and commonly by inserting a λDE3 prophage expressing the required phage polymerase into the host strain to create lysogenic host strains. The T7 RNA polymerase can also be delivered to the cell by infection with a specialised λ transducing phage that carries the gene for the T7 RNA polymerase.

Operator sequences which may be employed in the expression vector according to the present invention include lac, gal, deo and gln. One or more perfect palindrome operator sequences may be employed. In many preferred embodiments, two perfect palindrome operator sequences are employed, most advantageously one operator sequence being located downstream of the promoter, and one operator sequence being located upstream of the promoter. When two operator systems are employed, the operator sequences are preferably spaced to maximise control of the promoter. In many embodiments, the spacing is from 85 to 150 base pairs apart, preferably from 90 to 126 base pairs apart, and most preferably 91 or 92 base pairs apart. In certain embodiments, an operator sequence overlaps with the transcriptional start point.

It will be recognised that the operator system is commonly employed with an appropriate repressor sequence. Repressor sequences produce repressor protein, for example lacI gene sequence when using the lac operators. Other lac repressor sequences may also be used, for example the lacI$^Q$ sequence can be used to increase the level of lac repressor protein. The repressor sequence may also be provided by the host cell genome or by using an additional compatible plasmid.

The expression vector may be integrated into the host cell genome, but is preferably comprised within an extrachromosomal element such as a plasmid. Alternatively, the expression vector may be incorporated into phage or viral vectors and these used to deliver the expression system into the host cell system. The expression vectors can be assembled by methods known in the art.

The expression vector, particularly when the vector comprises a plasmid, typically also comprises one or more of the following: a selectable marker, for example a sequence conferring antibiotic resistance, and a cer stability sequence.

The expression vector of the present invention can be employed to express polypeptides, especially proteins in prokaryotic host cells. Examples of prokaryotic cells include bacterial cells, for example gram-negative bacterial cells, including *E. coli, Salmonella typhimurium, Serratia marsescens, Pseudomonas putida* and *Pseudomonas aeruginosa*, and gram-positive bacterial cells including *Bacillus subtilis*. Preferred host cells are bacteria, particularly enterobacteriacae, preferably *E coli*, and especially B or K12 strains thereof.

The expression vector of the present invention is commonly employed in the form of a plasmid. The plasmids may be autonomously replicating plasmids or integrative plasmids.

The expression vector of the present invention is advantageously employed for the manufacture of polypeptides, especially recombinant proteins, by culturing recombinant cells.

Polypeptides which can be expressed by the process of the present invention include therapeutic proteins and peptides, including cytokines, growth factors, antibodies, antibody fragments, immunoglobulin like polypeptides, enzyme, vaccines, peptide hormones, chemokines, receptors, receptor fragments, kinases, phosphatases, isomerases, hydrolyases, transcription factors and fusion polypeptides.

Antibodies which can be expressed include monoclonal antibodies, polyclonal antibodies and antibody fragments having biological activity, including multivalent and/or multispecific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain (V$_H$) connected to a light chain variable domain (V$_L$), in the same polypeptide chain; and (x) so-called linear antibodies comprising a pair of tandem Fd segments which, together with complementary light chain polypeptides, form a pair of antigen binding regions.

Preferred antibody fragments that can be prepared are mammalian single variable domain antibodies, being an antibody fragment comprising a folded polypeptide domain which comprises sequences characteristic of immunoglobulin variable domains and which specifically binds an antigen (i.e., dissociation constant of 500 nM or less, such as 400 nM or less, preferably 250 nM or less, and most preferably 100 nM or less), and which binds antigen as a single variable domain; that is, without any complementary variable domain. Single variable domain antibodies include complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains. Preferred single variable domains which can be prepared are selected from the group of V$_H$ and V$_L$, including Vkappa and Vlambda. Most preferably the single variable domains are human or camelid domains, including humanised camelid domains.

Where the target polypeptide comprises two or more chains to be secreted, particularly where the target polypeptide is a fragment antibody comprising two or more chains, each of the chains is attached to a secretion leader according to the present invention, and polynucleotides encoding such polypeptides are designed accordingly. The secretion leaders employed may be the same or different.

Accordingly, the present invention also provides a method for the production of a target polypeptide which comprises expressing a vector according to the first aspect of the present invention in a prokaryotic host cell.

The expression system is expressed by methods well known in the art for the cells employed. Preferred expression methods include culturing the host cells in growth medium, especially by fermentation, and then recovering the expressed polypeptide. The term "growth medium" refers to a nutrient medium used for growing the host cells. In many embodiments, a nutrient solution is employed. Suitable growth media for given host cells and methods of recovering polypeptides are well known in the art.

Expression may be induced by the addition of an inducer such as isopropyl-β-D-1-thiogalactopyranoside (IPTG), analogues of IPTG such as isobutyl-C-galactoside (IBCG), lactose or melibiose. Other inducers may be used and are described more fully elsewhere (e.g. see The Operon, eds Miller and Renznikoff (1978)). Inducers may be used individually or in combination.

Preferably, the signal peptide sequence is attached to the N-terminus of the recombinant polypeptide. In certain embodiments, the recombinant polypeptide comprises an N-terminal tag, the signal peptide sequence being attached to the tag, preferably to the N-terminus of the tag.

Polypeptides comprising signal peptides with amino acid sequences (SEQ ID NO 1), (SEQ ID NO 2), (SEQ ID NO 3), (SEQ ID NO 4) or (SEQ ID NO 5), or a functional equivalent thereof, attached to a recombinant polypeptide form another aspect of the present invention.

Preferably, the signal peptide sequence is attached to the N-terminus of the target polypeptide. In certain embodiments, the linkage between the secretion leader sequence and the polynucleotide encoding the target polypeptide is such that the target polypeptide comprises an N-terminal tag, the signal peptide sequence being attached to the tag, preferably to the N-terminus of the tag.

Polypeptides comprising signal peptides with amino acid sequences (SEQ ID NO 1), (SEQ ID NO 2), (SEQ ID NO 3), (SEQ ID NO 4) or (SEQ ID NO 5), or a functional equivalent thereof, attached to a recombinant target polypeptide form another aspect of the present invention.

The present invention is illustrated without limitation by the following examples.

EXAMPLE 1

TAR1-5-19 is an anti-TNF single domain V$_L$ antibody. The amino acid sequence was obtained from International patent application WO2005/035572.

Construction of Strains

Strain 1

A polynucleotide having the sequence:

(SEQ ID NO: 11)
CAT<u>ATGCTGAAACGTTCTTCTTGGCTGGCAACTCTGGGTCTGCTGACT

GTTGCATCCGTAAGCACTATTGTGTATGC</u>AGACATCCAAATGACCCAG

TCCCCTTCTTCTCTGAGCGCGTCTGTGGGTGATCGTGTGACCATCACT

TGCCGTGCTTCTCAATCCATCGATTCCTACCTGCACTGGTATCAACAG

AAACCAGGCAAGGCGCCGAAACTGCTGATTTACTCCGCGTCTGAGCTG

CAGTCTGGTGTGCCGAGCCGTTTCTCTGGCTCTGGTTCCGGTACCGAC

TTCACTCTGACCATCTCTTCTCTGCAGCCGGAGGATTTCGCAACTTAC

TACTGCCAACAAGTCGTGTGGCGTCCGTTTACCTTCGGTCAGGGCACG

AAAGTGGAAATTAAACGTTGATGACTCGAG (where the underlined nucleotides indicate the polynucleotide encoding for the eukaryotic signal peptide sequence MLKRSSWLATLGLLTVASVSTIVYA (SEQ ID NO 1)) was prepared as an NdeI/XhoI fragment. This fragment was cloned into vector pAVE011, prepared as described in International patent application WO 2007/088371, using the Nde I and Xho I restriction sites in the vector. Recombinant clones were identified by restriction digest and confirmed by sequencing. One plasmid clone was transformed into E. coli strain W3110. An equal amount of overnight culture was mixed with 40% glycerol and aliquoted into cryovials for storage at −70° C.

Strain 2

Strain 2 was prepared by the method for Strain 1, except that the polynucleotide prepared had the sequence:

(SEQ ID NO: 12)
CAT<u>ATGAAGAAAGCTACGTTTATTACTTGCCTGCTGGCTGTTCTGCTG

GTTTCTAACCCGATCGTTGTTAACGCGG</u>ATATCCAAATGACCCAGTCC

CCGAGCTCCCTGTCTGCCAGCGTTGGTGACCGCGTGACTATCACCTGC

CGCGCCAGCCAGTCTATTGATTCCTACCTGCATTGGTATCAGCAGAAA

CCGGGCAAAGCGCCGAAACTGCTGATCTATTCCGCCAGCGAGCTGCAG

TCTGGCGTTCCGAGCCGCTTCTCTGGTTCTGGCTCTGGTACTGACTTC

ACCCTGACCATCTCCTCCCTGCAGCCGGAAGACTTCGCTACCTATTAT

TGCCAACAGGTGGTTTGGCGTCCATTCACTTTTGGTCAGGGCACCAAA

GTAGAAATCAAACGTTAATAACTCGAG where the underlined nucleotides indicate the polynucleotide encoding for the eukaryotic signal peptide sequence MKKATFITCLLAVLLVSNPIWNA (SEQ ID NO 2).

Strain 3

Strain 3 was prepared by the method for Strain 1, except that the polynucleotide prepared had the sequence:

(SEQ ID NO: 13)
CAT<u>ATGAAAGTGTCTGCGGCCGCACTGGCAGTAATCCTGATCGCAACT</u>

<u>GCGCTGTGCGCGCCAGCCAGCGC</u>AGACATCCAGATGACGCAATCTCCG

TCTAGCCTGTCCGCGTCCGTGGGCGATCGCGTAACCATTACCTGCCGC

GCATCCCAGTCCATCGACAGCTATCTGCACTGGTATCAGCAGAAACCG

GGTAAAGCCCCGAAACTGCTGATCTATTCCGCTAGCGAACTGCAGAGC

GGCGTTCCGAGCCGTTTCTCCGGCTCTGGTTCTGGTACTGATTTTACC

CTGACCATCAGCTCTCTGCAACCGGAAGATTTTGCAACTTATTATTGT

CAGCAGGTGGTTTGGCGTCCGTTTACCTTCGGCCAGGGCACCAAAGTC

GAGATCAAACGTTGATGACTCGAG where the underlined nucleotides indicate the polynucleotide encoding for the eukaryotic signal peptide sequence MKVSAAALAVILIATALCAPASA (SEQ ID NO 3).

Strain 4

Strain 4 was prepared by the method for Strain 1, except that the polynucleotide prepared had the sequence:

(SEQ ID NO: 14)
CAT<u>ATGAAACTGCTGCTGCTGTCTGCTCTGCTGGGTTGTCTGGCTACT</u>

<u>GCGTATGCC</u>GATATCCAAATGACTCAGTCTCCGTCCTCCCTGTCTGCA

AGCGTGGGCGATCGTGTCACTATCACCTGCCGTGCGAGCCAGTCTATC

AGACTCTTACCTGCATTGGTACCAGCAAAACCGGGCAAAGCTCCTAAA

CTGCTGATCTACTCCGCGTCTGAACTGCAGTCTGGCGTTCCGTCTCGT

TTCTCTGGCAGCGGTAGCGGCACTGACTTTACCCTGACCATCTCCTCC

CTGCAGCCAGAAGATTTTGCGACTTACTATTGCCAGCAGGTGGTGTGG

CGCCCGTTCACCTTCGGTCAGGGCACCAAGGTGGAAATTAAGCGTTGA

TAACTCGAG where the underlined nucleotides indicate the polynucleotide encoding for the eukaryotic signal peptide sequence MKLLLLSALLGCLATAYA (SEQ ID NO 15).

Strain 5

Strain 5 was prepared by the method for Strain 1, except that the polynucleotide prepared had the sequence:

(SEQ ID NO: 16)
CAT<u>ATGAAAGTTTCTACTGCATTTCTGTGTCTGCTGCTGACTGTTAGC</u>

<u>GCATTCTCCGCTCAGGTCCTGGCC</u>GATATCCAGATGACGCAGTCCCCT

GTCCTCTCTGAGCGCCAGCTAGGTGATCGCGTAACCATCACGTGCCGT

GCATCTCAGAGCATTGATTCTTATCTGCATTGGTACCAGCAGAAGCCG

GGCAAAGCGCCGAAACTGCTGATCTATAGCGCTTCCGAGCTGCAGTCC

GGTGTACCGTCTCGTTTTTCCGGTTCTGGCAGCGGTACCGATTTCACC

CTGACCATCTCCAGCCTGCAGCCGGAGGATTTCGCGACTTATTACTGC

CAGCAGGTTGTCTGGCGTCCGTTCACCTTTGGTCAGGGCACGAAAGTT

GAAATCAAACGCTGATAACTCGAG where the underlined nucleotides indicate the polynucleotide encoding for the eukaryotic signal peptide sequence MKVSTAFLCLLLTVSAFSAQVLA (SEQ ID NO 4).

Strain 6

Strain 6 was prepared by the method for Strain 1, except that the polynucleotide prepared had the sequence:

(SEQ ID NO: 17)
CAT<u>ATGAAAGTTTCTGCTGCTCTGCTGTGGCTGCTGCTGATTGCTGCT</u>

<u>GCTTTCTCTCCGCAGGGTCTGGCC</u>GATATCCAGATGACTCAGTCCCCA

TCTAGCCTGAGCGCGTCTGTGGGCGACCGTGTGACTATCACCTGCCGT

GCGAGCCAGTCTATCGACTCCTACCTGCATTGGTATCAGCAGAAACCG

GGTAAAGCTCCGAAACTGCTGATTTACTCCGCTTCCGAACTGCAGTCT

GGCGTACCATCTCGCTTCTCTGGCAGCGGCTCCGGCACCGACTTTACC

CTGACTATCTCCTCTCTGCAGCCGGAGGATTTCGCAACGTATTATTGT

CAGCAAGTCGTTTGGCGCCCTTTCACCTTCGGTCAGGGCACCAAAGTG

GAGATCAAGCGTTGATAACTCGAG where the underlined nucleotides indicate the polynucleotide encoding for the eukaryotic signal peptide sequence MKVSAALLWLLLIAAAFSPQGLA (SEQ ID NO 18).

Strain 7

Strain 7 was prepared by the method for Strain 1, except that the polynucleotide prepared had the sequence:

(SEQ ID NO: 19)
CAT<u>ATGAAAGCGTTTCCAACCTTCGCACTGCTGTTTCTGGTTCTGCTG</u>

<u>TTTTCCGCTCACGTTAGCGATGCT</u>GATATCCAAATGACCCAGAGCCCA

AGCTCTCTGTCCGCAAGCGTAGGTGACCGTGTTACGATCACCTGCCGT

GCGAGCCAGTCTATCGATTCCTACCTGCACTGGTATCAGCAGAAGCCA

GGCAAGGCTCCGAAACTGCTGATCTACTCTGCTTCCGAGCTGCAGTCC

GGCGTTCCGTCTCGCTTCTCCGGTTCTGGCTCCGGTACCGACTTCACG

CTGACCATCTCTTCTCTGCAGCCGGAAGACTTCGCTACTTACTACTGT

CAGCAGGTTGTTTGGCGTCCGTTTACTTTCGGCCAGGGTACCAAAGTA

GAAATCAAACGTTAATAACTCGAG where the underlined nucleotides indicate the polynucleotide encoding for the eukaryotic signal peptide sequence MKAFPTFALLFLVLLFSAHVSDA (SEQ ID NO 20).

Strain 8

Strain 8 was prepared by the method for Strain 1, except that the polynucleotide prepared had the sequence:

(SEQ ID NO: 21)
CAT<u>ATGAAATGTCTGCTGCTGGCGCTGGGTCTGGCACTGGCATGTGCG</u>
<u>GCACAGGCG</u>GACATCCAGATGACGCAGTCTCCATCTAGCCTGTCTGCT
TCCGTTGGCGATCGTGTTACCATCACCTGCCGTGCCAGCCAGTCTATC
GATTCTTACCTGCACTGGTATCAGCAGAAACCGGGTAAAGCGCCGAAG
CTGCTGATCTATTCTGCCTCCGAGCTGCAGAGCGGTGTGCCGTCTCGC
TTCTCTGGCTCTGGTTCTGGTACTGACTTTACGCTGACGATTAGCTCC
CTGCAGCCGGAGGACTTCGCGACCTATTACTGCCAGCAGGTTGTATGG
CGTCCGTTCACGTTCGGCCAGGGTACCAAAGTTGAAATCAAGCGTTAA
TAACTCGAG where the underlined nucleotides indicate the polynucleotide encoding for the eukaryotic signal peptide sequence MKCLLLALGLALACAAQA (SEQ ID NO 5).

Shake-Flask Evaluation

10 μl of the thawed glycerol stock was inoculated into 5 ml Luria Broth (LB, 5 g/L yeast extract, 10 g/L tryptone, and 5 g/L sodium chloride) supplemented with tetracycline (10 μg/ml) and glucose (1 g/L). This was incubated at 37° C. in an orbital shaker for 16 h. 500 μl of this culture was then used to inoculate two 250 ml Erlenmeyer flasks containing 50 ml of Luria Broth (composition as described above). The flasks were incubated at 37° C., at 200 rpm in an orbital shaker. Growth was monitored until OD600=0.5-0.7. At this point one flask was induced with IPTG (isopropyl-.β.-D-1-thiogalactopyranoside) to a final concentration 0.1 mM whilst the second flask was left un-induced and the incubation continued, under the conditions described above for 22 hours, during which samples were taken for measurement of growth, and accumulation of TAR1-5-19 within the bacterial cells. The accumulation levels of TAR1-5-19 was determined using SimplyBlue stained SDS-PAGE gels of whole cell lysates of the sampled bacteria. The harvested cells were further subjected to osmotic shock cell fractionation to isolate the cellular fraction containing proteins that had partitioned in the soluble E. coli periplasmic fraction and the accumulation level in different fractions determined using SimplyBlue stained SDS-PAGE gels. The OS1 (OS=Osmotic Shock) fraction is the supernatant recovered after washing harvested cells in buffer containing sucrose, the OS2 fraction is the supernatant recovered after washing with a low ionic strength buffer, the 'supernatant/growth' medium is the residual cell-free residual growth medium and the 'cell pellet' is the cell pellet after osmotic shock fractionation. Correctly secreted target polypeptide is detected in the OS1 and/or the OS2 and/or the supernatant/growth medium fractions.

FIG. 1 shows shake-flask data for Strain 1. It can be seen that a secreted protein of the expected molecular weight was detected in the osmotic shock fractions. This band was subsequently confirmed to be TAR1-5-19 by N-terminal amino acid sequencing. Low level partitioning of TAR1-5-19 into the growth medium was also evident (Lane 2).

FIG. 2 shows shake-flask data for Strain 2. It can be seen that a secreted protein of the expected molecular weight was detected in the osmotic shock fractions. This band was subsequently confirmed to be TAR1-5-19 by N terminal amino acid sequencing.

FIG. 3 shows shake-flask data for Strain 3. It can be seen that a secreted protein of the expected molecular weight was detected in the osmotic shock fractions.

Strain 4 did not accumulate any secreted protein detectable using SimplyBlue stained SDS-PAGE gels.

FIG. 4 shows shake-flask data for Strain 5 and Strain 6. It can be seen that a secreted protein of the expected molecular weight was detected in the osmotic shock fractions for Strain 5 (according to the present invention), but not Strain 6.

FIG. 5 shows shake-flask data for Strain 7 and Strain 8. It can be seen that a secreted protein of the expected molecular weight was detected in the osmotic shock fractions, and the growth medium, for Strain 8 (according to the present invention), but not Strain 7.

FERMENTER EVALUATION OF STRAINS 1 AND 2

Fermentation inocula for each of Strains 1 and 2 were raised by adding 200 μl of glycerol stock to a 2.0 L baffled shake flask containing 200 mL of Luria Broth (LB) containing 5 g/L yeast extract, 10 g/L peptone, 10 g/L sodium chloride, 10 g/L glucose and 15 mg/L tetracycline. Inocula were grown for 10 h at 37° C. in a shaker-incubator with an agitation of 200 rpm. 20 ml of shake flask inoculum was used to inoculate a 5 L working volume fermenter containing 4 L of batch growth medium (or 45 ml of shake flask inoculum was used to inoculate a 15 L working volume fermenter containing 9 L of batch growth medium for Strain 3). The fermentation was carried out under the operating conditions described below. Temperature was controlled at 37° C. for the first 7-7.5 hours then reduced to 30° C. over a 2 hour period and controlled at 30° C. for the remainder of the fermentation. pH was controlled at 7.0 by automatic addition of 25% (w/v) ammonium hydroxide. The dissolved oxygen tension (dOT) set point was 30% of air saturation and was controlled by automatic adjustment of the fermenter stirrer speed, from a minimum of 250 rpm up to a maximum of 1500 rpm, and supplementation of oxygen to the inlet gas stream. Airflow to the fermenter vessel was 0.5 v/v/min throughout.

The composition of the batch growth medium is provided in Table 1.

TABLE 1

| Component | Final concentration [g/L], [mg/L] and [ml/L] of purified water |
|---|---|
| $(NH_4)_2SO_4$ | 10.0 g/L |
| Glycerol | 35.0 g/L |
| Yeast extract | 20.0 g/L |
| $NaH_2PO_4$ | 6.0 g/L |
| $KH_2PO_4$ | 3.0 g/L |
| NaCl | 0.5 g/L |
| $MgSO_4 \cdot 7H_2O$ | 0.5 g/L |
| $CaCl_2 \cdot 2H_2O$ | 30 mg/L |
| Antifoam DF204 | 0.4 ml/L |
| Tetracycline | 15 mg/L |
| $FeCl_3 \cdot 6H_2O$ | 140 mg/L |

TABLE 1-continued

| Component | Final concentration [g/L], [mg/L] and [ml/L] of purified water |
|---|---|
| ZnSO₄•7H₂O | 75 mg/L |
| MnSO₄•H₂O | 26 mg/L |
| Na₂MoO₄•2H₂O | 6 mg/L |
| CuSO₄•5H₂O | 7 mg/L |
| H₃•BO₃ | 2 mg/L |
| CoCl₂•6H₂O | 6 mg/L |

The composition of the glycerol/ammonium sulphate feed is provided in Table 2.

TABLE 2

| Component of Feed | Amount required [g/L] of purified water |
|---|---|
| Glycerol | 714 |
| (NH₄)₂SO₄ | 75 |

Fermentations were performed in batch mode until depletion of the carbon source (i.e. glycerol) which occurred ca. 10 h post inoculation and was characterized by a sharp rise in dOT. Fed-batch fermentation was initiated at the point of carbon source exhaustion by the addition of a glycerol/ammonium sulphate feed at a feed rate of 2.6-2.9 g of feed per L of medium per hr. Induction was carried out by addition of IPTG to a final concentration of 0.125 mM once the biomass level in the fermentation reached OD600=45-55. The fed-batch phase was continued for 46 hr post induction. The cells and residual cell free growth medium were then harvested. The harvested cells were further subjected to osmotic shock cell fractionation to isolate the cellular fraction containing proteins that had partitioned in the soluble *E. coli* periplasmic fraction.

The accumulation of TAR1-5-19 in the soluble periplasmic extract and residual growth medium was estimated as described above. High level secretion of TAR-5-19 was achieved. FIG. 6 shows the data from Strain 1. It can be seen that TAR1-5-19 is secreted and accumulated in the growth medium (S/N). The titre was estimated to be 400 mg/L culture. FIG. 7 shows the data for Strain 2. It can be seen that TAR1-5-19 is secreted and accumulated in the growth medium (S/N). The titre was estimated to be 2400 mg/L culture. The residual pellet fraction following release of the periplasmic fraction (FIG. 6, Lane 9) indicates the accumulation of TAR1-5-19 with the secretion leader. It will be evident to those skilled in the art that further optimisation of the fermentation and induction conditions would increase the secretion of TAR1-5-19 yet further increasing the titre.

EXAMPLE 2

The ability of vectors according to the present invention to secrete *E coli* thioredoxin was investigated. It has been shown that this protein does not secrete very efficiently using typical sec pathway leader sequences such as phoA, due to its rapid folding in the cytoplasm (JOURNAL OF BACTERIOLOGY, October 2003, p. 5706-5713). We compared the secretion of thioredoxin by the present invention with secretion using dsbA and ompA secretion leaders, both of which have been demonstrated to secrete thioredoxin.

The following gene was synthesised, consisting of the coding sequence for the leader having SEQ ID NO 4 attached directly to thioredoxin:

```
                                          (SEQ ID NO 22)
CATATGAAAGTTTCTACTGCATTTCTGTGTCTGCTGCTGACTGTTAGC

GCATTCTCCGCTCAGGTCCTGGCCAGCGATAAAATTATTCACCTGACT

GACGAGAGTTTTGACACGGATGTACTCAAAGCGGACGGGGCGATCCTC

GTCGATTTCTGGGCAGAGTGGTGCGGTCCGTGCAAAATGATCGCCCCG

ATTCTGGATGAAATCGCTGACGAATATCAGGGCAAACTGACCGTTGCA

AAACTGAACATCGATCAAAACCCTGGCACTGCGCCGAAATATGGCATC

CGTGGTATCCCGACTCTGCTGCTGTTCAAAAACGGTGAAGTGGCGGCA

ACCAAAGTGGGTGCACTGTCTAAAGGTCAGTTGAAAGAGTTCCTCGAC

GCTAACCTGGCGTAACTCGAG
```

Construction of Plasmid pAB222 and Strain 9 pAB222 was prepared by the method given for Strain 1, except that SEQ ID NO 22 was employed, and transformed into *E. coli* strain W3110, also by the method for Strain 1, to generate Strain 9. Similar constructs were made as controls, which coded for thioredoxin using the dsbA (Strain 10) and ompA (Strain 11) secretion leader sequences.

Shake-Flask Evaluation

Shake flask evaluations of Strains 9, 10 and 11 were carried out by the method given in Example 1, and the results shown in FIG. 8.

The data shows that Strain 9 secretes more thioredoxin into the periplasm than comparative Strains 10 and 11.

EXAMPLE 3

The ability of vectors according to the present invention to secrete Human growth hormone (hGH) was investigated. hGH has been shown to be secreted at higher levels with a dsbA leader, which is thought to be an srp dependent secretion leader, compared with ompA (Protein Engineering vol. 16 no. 12 pp. 1131-1138, 2003).

The following gene was synthesised, consisting of the coding sequence for the leader having SEQ ID NO 4 attached to hGH coding region.

```
                                          (SEQ ID NO 23)
CATATGAAAGTTAGCACCGCGTTTCTGTGCTTGCTGTTGACCGTTTCC

GCTTTTAGCGCACAAGTCCTGGCCTTTCCTACGATTCCGCTGTCTCGT

CTGTTTGATAATGCGATGCTGCGTGCCCATCGTTTGCACCAACTGGCG

TTTGACACTTACCAGGAGTTTGAGGAGGCGTATATCCCGAAAGAGCAG

AAGTATAGCTTCCTGCAAAACCCGCAAACCAGCCTGTGCTTCAGCGAG

TCTATTCCAACCCCGTCTAACCGTGAAGAAACGCAGCAAAAGTCCAAT

TTGGAACTGCTGCGCATTAGCCTGCTGCTGATCCAGAGCTGGCTGGAG

CCGGTGCAGTTCCTGCGCAGCGTCTTTGCGAACTCCTTGGTGTACGGC

GCAAGCGACAGCAATGTGTACGATCTGCTGAAGGACCTGGAAGAGGGT
```

```
-continued
ATTCAGACGTTGATGGGTCGCCTGGAAGATGGTTCGCCGCGTACCGGC

CAAATCTTCAAGCAAACGTATAGCAAGTTCGATACCAATAGCCACAAT

GACGACGCTCTGCTGAAAAACTACGGCCTGCTGTATTGCTTCCGCAAA

GATATGGACAAAGTCGAAACCTTCCTGCGTATTGTGCAGTGTCGTTCC

GTTGAAGGTAGCTGTGGTTTCTAACTCGAG
```

Strain 12 was prepared by the method given for Strain 1, except that SEQ ID NO 23 was employed and transformed into *E. coli* strain W3110.

Shake-Flask Evaluation

Shake flask evaluation of Strain 12 was carried out by the method given in Example 1, and the results shown in FIG. 9.

The data shows that hGH is successfully secreted by Strain 12. After 22 hours incubation post-induction, hGH secretion into the periplasm and its accumulation in both the osmotic shock fractions (OS1 and OS2) is clearly evident using SimplyBlue stained SDS-PAGE gels.

EXAMPLE 4

The following gene was synthesised, comprising a D1.3 Fab sequence in which both the light and heavy chains were linked to coding sequences for the leader having SEQ ID NO 4:

```
                                          (SEQ ID NO 24)
CATATGAAAGTGAGCACCGCGTTTCTGTGTCTGCTGTTGACGGTGTCT

GCGTTTTCCGCACAAGTCCTGGCGCAAGTTCAACTGCAGGAAAGCGGT

CCGGGTCTGGTCGCGCCGAGCCAGAGCTTGAGCATCACCTGCACCGTG

TCCGGCTTCAGCCTGACCGGCTATGGTGTGAATTGGGTTCGCCAGCCA

CCGGGTAAGGGTCTGGAGTGGTTGGGTATGATTTGGGGTGATGGCAAC

ACGGACTATAACAGCGCCCTGAAGAGCCGCCTGAGCATCAGCAAGGAC

AATAGCAAATCGCAGGTGTTTCTGAAGATGAATAGCTTGCACACCGAC

GATACGGCCCGTTACTATTGTGCACGTGAGCGTGACTATCGTCTGGAT

TACTGGGGTCAGGGTACCACCGTTACCGTGAGCAGCGCTTCCACCAAG

TGGCCCGAGCGTGTTCCCGCGGCCCCGAGCTCTAAGAGCACGAGCGGC

GGTACTGCTGCGCTGGGCTGTCTGGTCAAAGATTACTTCCCGGAACCG

GTCACCGTGTCTTGGAACAGCGGCGCACTGACCAGCGGCGTTCATACC

CCTGCGGTGCTGCAAAGCTCGGGCCTGTACAGCCTGAGCTCTGTTGTC

ACTGTTCCGAGCAGCAGCCTGGGTACGCAGACGTACATTTGCAATGTT

AATCACAACCCGTCCAACACGAAAGTCGATAAGAAGGTCGAACCGAAG

TCCACCAAAACCCATACCTCCGGTGGTGAGCAAAAACTGATTTCGGAG

GAGGACCTGAACTAATAAGTCGACGCTAGCGGATCCAAGGAGACTAGT

CATATGAAAGTGAGCACCGCGTTCCTGTGCCTGTTGCTGACGGTCAGC

GCCTTCAGCGCTCAAGTTCTGGCGGACATTGAGCTGACTCAGAGCCCA

GCGAGCCTGAGCGCCAGCGTCGGTGAAACCGTGACCATTACGTGTCGC

GCAAGCGGCAACATTCACAACTACCTGGCATGGTATCAGCAAAAACAA

GGCAAAAGCCCTCAACTGCTGGTTTACTATACGACCACCCTGGCGGAT
```

```
-continued
GGCGTTCCGAGCCGTTTCTCTGGTTCCGGCTCCGGCACGCAATACTCC

TTGAAGATCAATAGCCTGCAGCCGGAAGCGTTTGGTAGCTACTATTGC

CAGCACTTTTGGTCTACCCCGCGTACCTTTGGTGGCGGTACCAAGCTG

GAAATCAAACGTACGGTTGCAGCGCCGTCCGTGTTCATCTTTCCGCCG

AGCGACGAGCAACTGAAGAGCGGTACTGCCTCTGTGGTGTGCCTGCTG

AACAATTTCTACCCGCGTGAAGCGAAGGTTCAGTGGAAAGTCGATAAC

GCTTTGCAGTCTGGTAATAGCCAAGAGAGCGTGACCGAGCAGGACAGC

AAAGATAGCACCTATTCCCTGAGCAGCACCCTGACGCTGAGCAAGGCG

GACTACGAAAAGCATAAGGTTTACGCATGTGAGGTCACGCATCAGGGT

CTGAGCTCGCCGGTCACCAAATCGTTCAATCGCGGCGAGTCCTAATAA

CTCGAG
```

Strain 13 was prepared by the method given for Strain 1, except that SEQ ID NO 24 was employed.

Shake-Flask Evaluation

Shake flask evaluation of Strain 13 was carried out by the method given in Example 1, except that no uninduced flask was employed. The accumulation of biologically active D1.3 Fab in the soluble periplasmic extract and residual growth medium was estimated by determining the binding of D1.3 Fab to lysozyme (antigen) in an ELISA assay by reference to a standard curve prepared with purified active D1.3 Fab. It was estimated that 1.2 µg/ml of active D1.3 was produced in the supernatant of these flasks. This demonstrated that the leader can be used for secretion of two separate polypeptide chains, which are subsequently able to form active material in the periplasm.

EXAMPLE 5

Preparation of Strain 14

Plasmid pAB222 (prepared by the method of Example 2) was used as the start point for construction of pAB270. The *Pseudomonas savastanoi* origin of replication was cloned using Polymerase Chain Reaction from Plasmid pCN60 (ATCC 77101; Nieto C, et al. (1990) Gene 87: 145-149). The primers used were F37a (Sequence: 5' AGATCTACGCT-TATGGGTGCCTTTCC (SEQ ID NO 25)) and B29a (Sequence: 5' AGATCTAATACGCAAACCGCCTCTCC (SEQ ID NO 26). The PCR product was cloned into TOPO TA pCR2.1 (Invitrogen) and then into pAVE187 by BgI II digestion from pCR2.1. The resultant plasmid, pAB270, was transformed into *Pseudomonas putida* NCIMB 12018 via electroporation to generate Strain 14.

Shake Flask Evaluation

10 µl of the thawed glycerol stock was inoculated into 5 ml Nutrient Broth (NB, Oxoid CM0001) supplemented with tetracycline (10 µg/ml). This was incubated at 29° C. in an orbital shaker for 16 h. 500 µl of this culture was then used to inoculate a 250 ml Erlenmeyer flask containing 50 ml of Nutrient Broth (composition as described above). The flask was incubated at 29° C., at 200 rpm in an orbital shaker. Growth was monitored until OD600=0.5-0.7. At this point the flask was induced with IPTG (isopropyl-.β.-D-1-thiogalactopyranoside) to a final concentration 0.1 mM and the incubation continued, under the conditions described above for 22 hours, during which samples were taken for measurement of growth, and accumulation of thioredoxin within the bacterial cells. The accumulation levels of thioredoxin was determined using SimplyBlue stained SDS-PAGE gels of whole cell lysates of the sampled bacteria. The harvested cells were further subjected to osmotic shock cell fractionation to isolate the cellular fraction containing proteins that had partitioned in the soluble periplasmic fraction.

The results are shown in FIG. 10 and demonstrate that thioredoxin was secreted by Strain 14.

The invention claimed is:

1. A prokaryotic expression vector comprising
   (a) a prokaryotic promoter operably linked to a heterologous polynucleotide encoding a target polypeptide operably linked to a polynucleotide encoding a eukaryotic secretion leader which is a signal peptide having an amino acid sequence at least 90% identical to SEQ ID NO: 4 and is having a function of secreting the target polypeptide to a periplasmic space of a prokaryotic host cell; and
   (b) at least one perfect palindrome operator sequence.

2. The prokaryotic expression vector according to claim 1, wherein the signal peptide has a sequence at least 95% identical to SEQ ID NO: 4.

3. The prokaryotic expression vector according to claim 2, wherein the polynucleotide encoding the target polypeptide operably linked to the eukaryotic secretion leader sequence has a structure such that a polynucleotide encoding the eukaryotic secretion leader sequence is attached at the 5' end of the polynucleotide encoding the target polypeptide.

4. The prokaryotic expression vector according to claim 3, wherein the expression vector is a plasmid and the target polypeptide is selected from the group consisting of cytokines, growth factors, antibodies, antibody fragments, immunoglobulin like polypeptides, enzyme, vaccines, peptide hormones, chemokines, receptors, receptor fragments, kinases, phosphatases, isomerases, hydrolyases, transcription factors and fusion polypeptides.

5. The prokaryotic expression vector according to claim 1, wherein the polynucleotide encoding the target polypeptide operably linked to the eukaryotic secretion leader sequence has a structure such that a polynucleotide encoding the eukaryotic secretion leader sequence is attached at the 5' end of the polynucleotide encoding the target polypeptide.

6. The prokaryotic expression vector according to claim 1, wherein the vector is a plasmid.

7. The prokaryotic expression vector according to claim 1, wherein the target polypeptide is selected from the group consisting of cytokines, growth factors, antibodies, antibody fragments, immunoglobulin like polypeptides, enzyme, vaccines, peptide hormones, chemokines, receptors, receptor fragments, kinases, phosphatases, isomerases, hydrolyases, transcription factors and fusion polypeptides.

8. The prokaryotic expression vector according to claim 1, wherein the eukaryotic secretion leader sequence encodes the signal peptide of SEQ ID NO: 4.

9. The prokaryotic expression vector according to claim 1, wherein the prokaryotic promoter is an *E. coli* RNA polymerase-based promoter system.

10. The prokaryotic expression vector according to claim 1, wherein the heterologous polynucleotide encoding the eukaryotic secretion leader comprises the nucleotide sequence from position 4 to position 72 of SEQ ID NO: 16.

11. The prokaryotic expression vector according to claim 1, wherein the signal peptide has the amino acid sequence of SEQ ID NO: 4.

12. A prokaryotic microorganism comprising the prokaryotic expression vector according to claim 1.

13. The prokaryotic microorganism according to claim 12, wherein the microorganism is selected from the group consisting of *E. coli, Salmonella typhimurium, Serratia marsescens, Pseudomonas putida, Pseudomonas aeruginosa,* and *Bacillus subtilis.*

14. A method for the production of a target polypeptide which comprises expressing the prokaryotic expression vector according to claim 1 in a prokaryotic host cell.

15. The method according to claim 14, wherein the prokaryotic host cell is selected from the group consisting of *E. coli, Salmonella typhimurium, Serratia marsescens, Pseudomonas aeruginosa, Pseudomonas putida* and *Bacillus subtilis.*

16. A method for producing a target polypeptide which comprises:
   a) culturing a prokaryotic host cell comprising the prokaryotic expression vector according to claim 1, thereby to express the target polypeptide, and
   b) recovering the target polypeptide.

* * * * *

SEQUENCE LISTING

<160> NUMBER OF SEQ ID NOS: 26

<210> SEQ ID NO 1
<211> LENGTH: 25
<212> TYPE: PRT
<213> ORGANISM: Porphyra purpurea

<400> SEQUENCE: 1

Met Leu Lys Arg Ser Ser Trp Leu Ala Thr Leu Gly Leu Leu Thr Val
1               5                   10                  15

Ala Ser Val Ser Thr Ile Val Tyr Ala
            20                  25

<210> SEQ ID NO 2
<211> LENGTH: 24
<212> TYPE: PRT
<213> ORGANISM: Porphyra purpurea

<400> SEQUENCE: 2

Met Lys Lys Ala Thr Phe Ile Thr Cys Leu Leu Ala Val Leu Leu Val
1               5                   10                  15

Ser Asn Pro Ile Val Val Asn Ala
            20

<210> SEQ ID NO 3
<211> LENGTH: 23
<212> TYPE: PRT
<213> ORGANISM: Homo sapiens

<400> SEQUENCE: 3

Met Lys Val Ser Ala Ala Ala Leu Ala Val Ile Leu Ile Ala Thr Ala
1               5                   10                  15

Leu Cys Ala Pro Ala Ser Ala
            20

<210> SEQ ID NO 4
<211> LENGTH: 23
<212> TYPE: PRT
<213> ORGANISM: Cavia porcellus

<400> SEQUENCE: 4

Met Lys Val Ser Thr Ala Phe Leu Cys Leu Leu Leu Thr Val Ser Ala
1               5                   10                  15

Phe Ser Ala Gln Val Leu Ala
            20

<210> SEQ ID NO 5
<211> LENGTH: 18
<212> TYPE: PRT
<213> ORGANISM: bubalus bubalis

<400> SEQUENCE: 5

Met Lys Cys Leu Leu Leu Ala Leu Gly Leu Ala Leu Ala Cys Ala Ala
1               5                   10                  15

Gln Ala

<210> SEQ ID NO 6
<211> LENGTH: 78
<212> TYPE: DNA
<213> ORGANISM: Artificial Sequence
<220> FEATURE:
<223> OTHER INFORMATION: Polynucleotide encoding Seq ID No. 1

<400> SEQUENCE: 6
catatgctga aacgttcttc ttggctggca actctgggtc tgctgactgt tgcatccgta     60
agcactattg tgtatgca                                                  78

<210> SEQ ID NO 7
<211> LENGTH: 75
<212> TYPE: DNA
<213> ORGANISM: Artificial Sequence
<220> FEATURE:
<223> OTHER INFORMATION: Polynucleotide encoding Seq ID No. 2

<400> SEQUENCE: 7
catatgaaga aagctacgtt tattacttgc ctgctggctg ttctgctggt ttctaacccg     60
atcgttgtta acgcg                                                     75

<210> SEQ ID NO 8
<211> LENGTH: 72
<212> TYPE: DNA
<213> ORGANISM: Artificial Sequence
<220> FEATURE:
<223> OTHER INFORMATION: Polynucleotide encoding Seq ID No. 3

<400> SEQUENCE: 8
catatgaaag tgtctgcggc cgcactggca gtaatcctga tcgcaactgc gctgtgcgcg     60
ccagccagcg ca                                                        72

<210> SEQ ID NO 9
<211> LENGTH: 72
<212> TYPE: DNA
<213> ORGANISM: Artificial Sequence
<220> FEATURE:
<223> OTHER INFORMATION: Polynucleotide encoding Seq ID No. 4

<400> SEQUENCE: 9
catatgaaag tttctactgc atttctgtgt ctgctgctga ctgttagcgc attctccgct     60
caggtcctgg cc                                                        72

<210> SEQ ID NO 10
<211> LENGTH: 57
<212> TYPE: DNA
<213> ORGANISM: Artificial Sequence
<220> FEATURE:
<223> OTHER INFORMATION: Polynucleotide encoding Seq ID No. 5

<400> SEQUENCE: 10
catatgaaat gtctgctgct ggcgctgggt ctggcactgg catgtgcggc acaggcg        57

<210> SEQ ID NO 11
<211> LENGTH: 414
<212> TYPE: DNA
<213> ORGANISM: Artificial Sequence
<220> FEATURE:
<223> OTHER INFORMATION: Polynucleotide used to prepare Strain 1

<400> SEQUENCE: 11

| | |
|---|---|
| catatgctga aacgttcttc ttggctggca actctgggtc tgctgactgt tgcatccgta | 60 |
| agcactattg tgtatgcaga catccaaatg acccagtccc cttcttctct gagcgcgtct | 120 |
| gtgggtgatc gtgtgaccat cacttgccgt gcttctcaat ccatcgattc ctacctgcac | 180 |
| tggtatcaac agaaaccagg caaggcgccg aaactgctga tttactccgc gtctgagctg | 240 |
| cagtctggtg tgccgagccg tttctctggc tctggttccg gtaccgactt cactctgacc | 300 |
| atctcttctc tgcagccgga ggatttcgca acttactact gccaacaagt cgtgtggcgt | 360 |
| ccgtttacct tcggtcaggg cacgaaagtg gaaattaaac gttgatgact cgag | 414 |

<210> SEQ ID NO 12
<211> LENGTH: 411
<212> TYPE: DNA
<213> ORGANISM: Artificial Sequence
<220> FEATURE:
<223> OTHER INFORMATION: Polynucleotide used to prepare Strain 2

<400> SEQUENCE: 12

| | |
|---|---|
| catatgaaga aagctacgtt tattacttgc ctgctggctg ttctgctggt ttctaacccg | 60 |
| atcgttgtta acgcggatat ccaaatgacc cagtccccga gctccctgtc tgccagcgtt | 120 |
| ggtgaccgcg tgactatcac ctgccgcgcc agccagtcta ttgattccta cctgcattgg | 180 |
| tatcagcaga aacgggcaa agcgccgaaa ctgctgatct attccgccag cgagctgcag | 240 |
| tctggcgttc cgagccgctt ctctggttct ggctctggta ctgacttcac cctgaccatc | 300 |
| tcctccctgc agccggaaga cttcgctacc tattattgcc aacaggtggt ttggcgtcca | 360 |
| ttcacttttg gtcagggcac caaagtagaa atcaaacgtt aataactcga g | 411 |

<210> SEQ ID NO 13
<211> LENGTH: 408
<212> TYPE: DNA
<213> ORGANISM: Artificial Sequence
<220> FEATURE:
<223> OTHER INFORMATION: Polynucleotide used to prepare Strain 3

<400> SEQUENCE: 13

| | |
|---|---|
| catatgaaag tgtctgcggc cgcactggca gtaatcctga tcgcaactgc gctgtgcgcg | 60 |
| ccagccagcg cagacatcca gatgacgcaa tctccgtcta gcctgtccgc gtccgtgggc | 120 |
| gatcgcgtaa ccattacctg ccgcgcatcc cagtccatcg acagctatct gcactggtat | 180 |
| cagcagaaac cgggtaaagc cccgaaactg ctgatctatt ccgctagcga actgcagagc | 240 |
| ggcgttccga ccgtttctc cggctctggt tctggtactg attttaccct gaccatcagc | 300 |
| tctctgcaac cggaagattt tgcaacttat tattgtcagc aggtggtttg gcgtccgttt | 360 |
| accttcggcc agggcaccaa agtcgagatc aaacgttgat gactcgag | 408 |

<210> SEQ ID NO 14
<211> LENGTH: 393
<212> TYPE: DNA
<213> ORGANISM: Artificial Sequence
<220> FEATURE:
<223> OTHER INFORMATION: Polynucleotide used to prepare Strain 4

<400> SEQUENCE: 14

| | |
|---|---|
| catatgaaac tgctgctgct gtctgctctg ctgggttgtc tggctactgc gtatgccgat | 60 |
| atccaaatga ctcagtctcc gtcctccctg tctgcaagcg tgggcgatcg tgtcactatc | 120 |
| acctgccgtg cgagccagtc tatcgactct acctgcatt ggtaccagca aaaaccgggc | 180 |
| aaagctccta aactgctgat ctactccgcg tctgaactgc agtctggcgt tccgtctcgt | 240 |

```
ttctctggca gcggtagcgg cactgacttt accctgacca tctcctccct gcagccagaa    300
gattttgcga cttactattg ccagcaggtg gtgtggcgcc cgttcacctt cggtcagggc    360
accaaggtgg aaattaagcg ttgataactc gag                                 393
```

<210> SEQ ID NO 15
<211> LENGTH: 18
<212> TYPE: PRT
<213> ORGANISM: Salmo salar

<400> SEQUENCE: 15

```
Met Lys Leu Leu Leu Leu Ser Ala Leu Leu Gly Cys Leu Ala Thr Ala
1               5                   10                  15

Tyr Ala
```

<210> SEQ ID NO 16
<211> LENGTH: 408
<212> TYPE: DNA
<213> ORGANISM: Artificial Sequence
<220> FEATURE:
<223> OTHER INFORMATION: Polynucleotide used to prepare Strain 5

<400> SEQUENCE: 16

```
catatgaaag tttctactgc atttctgtgt ctgctgctga ctgttagcgc attctccgct     60
caggtcctgg ccgatatcca gatgacgcag tccccttcct ctctgagcgc cagcgtaggt    120
gatcgcgtaa ccatcacgtg ccgtgcatct cagagcattg attcttatct gcattggtac    180
cagcagaagc cgggcaaagc gccgaaactg ctgatctata gcgcttccga gctgcagtcc    240
ggtgtaccgt ctcgtttttc cggttctggc agcggtaccg atttcaccct gaccatctcc    300
agcctgcagc cggaggattt cgcgacttat tactgccagc aggttgtctg gcgtccgttc    360
acctttggtc agggcacgaa agttgaaatc aaacgctgat aactcgag                 408
```

<210> SEQ ID NO 17
<211> LENGTH: 408
<212> TYPE: DNA
<213> ORGANISM: Artificial Sequence
<220> FEATURE:
<223> OTHER INFORMATION: Polynucleotide used to prepare Strain 6

<400> SEQUENCE: 17

```
catatgaaag tttctgctgc tctgctgtgg ctgctgctga ttgctgctgc tttctctccg     60
cagggtctgg ccgatatcca gatgactcag tccccatcta gcctgagcgc gtctgtgggc    120
gaccgtgtga ctatcacctg ccgtgcgagc cagtctatcg actcctacct gcattggtat    180
cagcagaaac cgggtaaagc tccgaaactg ctgatttact ccgcttccga actgcagtct    240
ggcgtaccat ctcgcttctc tggcagcggc tccggcaccg actttaccct gactatctcc    300
tctctgcagc cggaggattt cgcaacgtat tattgtcagc aagtcgtttg gcgccctttc    360
accttcggtc agggcaccaa agtggagatc aagcgttgat aactcgag                 408
```

<210> SEQ ID NO 18
<211> LENGTH: 23
<212> TYPE: PRT
<213> ORGANISM: Homo sapiens

<400> SEQUENCE: 18

```
Met Lys Val Ser Ala Ala Leu Leu Trp Leu Leu Leu Ile Ala Ala Ala
1               5                   10                  15
```

Phe Ser Pro Gln Gly Leu Ala
            20

<210> SEQ ID NO 19
<211> LENGTH: 408
<212> TYPE: DNA
<213> ORGANISM: Artificial Sequence
<220> FEATURE:
<223> OTHER INFORMATION: Polynucleotide used to prepare Strain 7

<400> SEQUENCE: 19

| | | |
|---|---|---|
| catatgaaag cgtttccaac cttcgcactg ctgtttctgg ttctgctgtt ttccgctcac | 60 |
| gttagcgatg ctgatatcca aatgacccag agcccaagct ctctgtccgc aagcgtaggt | 120 |
| gaccgtgtta cgatcacctg ccgtgcgagc cagtctatcg attcctacct gcactggtat | 180 |
| cagcagaagc caggcaaggc tccgaaactg ctgatctact ctgcttccga gctgcagtcc | 240 |
| ggcgttccgt ctcgcttctc cggttctggc tccggtaccg acttcacgct gaccatctct | 300 |
| tctctgcagc cggaagactt cgctacttac tactgtcagc aggttgtttg gcgtccgttt | 360 |
| actttcggcc agggtaccaa agtagaaatc aaacgttaat aactcgag | 408 |

<210> SEQ ID NO 20
<211> LENGTH: 23
<212> TYPE: PRT
<213> ORGANISM: Xenopus laevis

<400> SEQUENCE: 20

Met Lys Ala Phe Pro Thr Phe Ala Leu Leu Phe Leu Val Leu Leu Phe
1               5                   10                  15
Ser Ala His Val Ser Asp Ala
            20

<210> SEQ ID NO 21
<211> LENGTH: 393
<212> TYPE: DNA
<213> ORGANISM: Artificial Sequence
<220> FEATURE:
<223> OTHER INFORMATION: Polynucleotide used to prepare Strain 8

<400> SEQUENCE: 21

| | | |
|---|---|---|
| catatgaaat gtctgctgct ggcgctgggt ctggcactgg catgtgcggc acaggcggac | 60 |
| atccagatga cgcagtctcc atctagcctg tctgcttccg ttggcgatcg tgttaccatc | 120 |
| acctgccgtg ccagccagtc tatcgattct tacctgcact ggtatcagca gaaaccgggt | 180 |
| aaagcgccga gctgctgat ctattctgcc tccgagctgc agagcggtgt gccgtctcgc | 240 |
| ttctctggct ctggttctgg tactgacttt acgctgacga ttagctccct gcagccggag | 300 |
| gacttcgcga cctattactg ccagcaggtt gtatggcgtc cgttcacgtt cggccagggt | 360 |
| accaaagttg aaatcaagcg ttaataactc gag | 393 |

<210> SEQ ID NO 22
<211> LENGTH: 405
<212> TYPE: DNA
<213> ORGANISM: Artificial Sequence
<220> FEATURE:
<223> OTHER INFORMATION: Polynucleotide used to prepare Strain 9

<400> SEQUENCE: 22

| | | |
|---|---|---|
| catatgaaag tttctactgc atttctgtgt ctgctgctga ctgttagcgc attctccgct | 60 |
| caggtcctgg ccagcgataa aattattcac ctgactgacg agagttttga cacggatgta | 120 |

| | |
|---|---|
| ctcaaagcgg acggggcgat cctcgtcgat ttctgggcag agtggtgcgg tccgtgcaaa | 180 |
| atgatcgccc cgattctgga tgaaatcgct gacgaatatc agggcaaact gaccgttgca | 240 |
| aaactgaaca tcgatcaaaa ccctggcact gcgccgaaat atggcatccg tggtatcccg | 300 |
| actctgctgc tgttcaaaaa cggtgaagtg gcggcaacca agtgggtgc actgtctaaa | 360 |
| ggtcagttga aagagttcct cgacgctaac ctggcgtaac tcgag | 405 |

<210> SEQ ID NO 23
<211> LENGTH: 654
<212> TYPE: DNA
<213> ORGANISM: Artificial Sequence
<220> FEATURE:
<223> OTHER INFORMATION: Polynucleotide used to prepare Strain 12

<400> SEQUENCE: 23

| | |
|---|---|
| catatgaaag ttagcaccgc gtttctgtgc ttgctgttga ccgtttccgc ttttagcgca | 60 |
| caagtcctgg cctttcctac gattccgctg tctcgtctgt ttgataatgc gatgctgcgt | 120 |
| gcccatcgtt tgcaccaact ggcgtttgac acttaccagg agtttgagga ggcgtatatc | 180 |
| ccgaaagagc agaagtatag cttcctgcaa aacccgcaaa ccagcctgtg cttcagcgag | 240 |
| tctattccaa ccccgtctaa ccgtgaagaa acgcagcaaa agtccaattt ggaactgctg | 300 |
| cgcattagcc tgctgctgat ccagagctgg ctggagccgg tgcagttcct gcgcagcgtc | 360 |
| tttgcgaact ccttggtgta cggcgcaagc gacagcaatg tgtacgatct gctgaaggac | 420 |
| ctggaagagg gtattcagac gttgatgggt cgcctggaag atggttcgcc gcgtaccggc | 480 |
| caaatcttca gcaaacgta tagcaagttc gataccaata gccacaatga cgacgctctg | 540 |
| ctgaaaaact acggcctgct gtattgcttc cgcaaagata tggacaaagt cgaaaccttc | 600 |
| ctgcgtattg tgcagtgtcg ttccgttgaa ggtagctgtg gtttctaact cgag | 654 |

<210> SEQ ID NO 24
<211> LENGTH: 1542
<212> TYPE: DNA
<213> ORGANISM: Artificial Sequence
<220> FEATURE:
<223> OTHER INFORMATION: Polynucleotide used to prepare Strain 13

<400> SEQUENCE: 24

| | |
|---|---|
| catatgaaag tgagcaccgc gtttctgtgt ctgctgttga cggtgtctgc gttttccgca | 60 |
| caagtcctgg cgcaagttca actgcaggaa agcggtccgg gtctggtcgc gccgagccag | 120 |
| agcttgagca tcacctgcac cgtgtccggc ttcagcctga ccggctatgg tgtgaattgg | 180 |
| gttcgccagc caccgggtaa gggtctggag tggttgggta tgatttgggg tgatggcaac | 240 |
| acggactata cagcgccct gaagagccgc tgagcatca gcaaggacaa tagcaaatcg | 300 |
| caggtgtttc tgaagatgaa tagcttgcac accgacgata cggcccgtta ctattgtgca | 360 |
| cgtgagcgtg actatcgtct ggattactgg ggtcaggggta ccaccgttac cgtgagcagc | 420 |
| gcttccacca agggcccgag cgtgttcccg ctggccccga gctctaagag cacgagcggc | 480 |
| ggtactgctg cgctgggctg tctggtcaaa gattacttcc cggaaccggt caccgtgtct | 540 |
| tggaacagcg gcgcactgac cagcggcgtt cataccccctg cggtgctgca aagctcgggc | 600 |
| ctgtacagcc tgagctctgt tgtcactgtt ccgagcagca gcctgggtac gcagacgtac | 660 |
| atttgcaatg ttaatcacaa cccgtccaac acgaaagtcg ataagaaggt cgaaccgaag | 720 |
| tccaccaaaa cccatacctc cggtggtgag caaaaactga tttcggagga ggacctgaac | 780 |
| taataagtcg acgctagcgg atccaaggag actagtcata tgaaagtgag caccgcgttc | 840 |

```
ctgtgcctgt tgctgacggt cagcgccttc agcgctcaag ttctggcgga cattgagctg      900
actcagagcc cagcgagcct gagcgccagc gtcggtgaaa ccgtgaccat tacgtgtcgc      960
gcaagcggca acattcacaa ctacctggca tggtatcagc aaaaacaagg caaaagccct     1020
caactgctgg tttactatac gaccaccctg gcggatggcg ttccgagccg tttctctggt     1080
tccggctccg gcacgcaata ctccttgaag atcaatagcc tgcagccgga agcgtttggt     1140
agctactatt gccagcactt tggtctacc ccgcgtacct tggtggcgg taccaagctg      1200 gaaatcaaac gtacggttgc agcgccgtcc gtgttcatct ttccgccgag cgacgagcaa     1260
ctgaagagcg gtactgcctc tgtggtgtgc ctgctgaaca atttctaccc gcgtgaagcg     1320
aaggttcagt ggaaagtcga taacgctttg cagtctggta atagccaaga gagcgtgacc     1380
gagcaggaca gcaaagatag cacctattcc ctgagcagca ccctgacgct gagcaaggcg     1440
gactacgaaa agcataaggt ttacgcatgt gaggtcacgc atcagggtct gagctcgccg     1500
gtcaccaaat cgttcaatcg cggcgagtcc taataactcg ag                       1542

<210> SEQ ID NO 25
<211> LENGTH: 26
<212> TYPE: DNA
<213> ORGANISM: Artificial Sequence
<220> FEATURE:
<223> OTHER INFORMATION: Primer F37a

<400> SEQUENCE: 25
agatctacgc ttatgggtgc ctttcc                                           26

<210> SEQ ID NO 26
<211> LENGTH: 26
<212> TYPE: DNA
<213> ORGANISM: Artificial Sequence
<220> FEATURE:
<223> OTHER INFORMATION: Primer B29a

<400> SEQUENCE: 26
agatctaata cgcaaaccgc ctctcc                                           26
```